United States Patent
Oudshoorn (10) Patent No.: US 10,792,303 B2
(45) Date of Patent: Oct. 6, 2020

(54) COMPOSITIONS AND METHODS FOR INDUCING BEIGE OR BROWN FAT TISSUE

(71) Applicant: Logick Energetics, Leiden (NL)

(72) Inventor: Berendina Oudshoorn, Bergschenhoek (NL)

(73) Assignee: Logick Energetics, Leiden (NL)

( * ) Notice: Subject to any disclaimer, the term of this patent is extended or adjusted under 35 U.S.C. 154(b) by 0 days.

(21) Appl. No.: 16/008,771

(22) Filed: Jun. 14, 2018

(65) Prior Publication Data
US 2018/0344761 A1  Dec. 6, 2018

Related U.S. Application Data

(63) Continuation of application No. PCT/NL2016/050871, filed on Dec. 14, 2016.

(30) Foreign Application Priority Data

Dec. 14, 2015 (NL) .................................. 2015957

(51) Int. Cl.
| | | |
|---|---|---|
| A61K 31/726 | (2006.01) | |
| A61P 3/04 | (2006.01) | |
| A61P 3/10 | (2006.01) | |
| A61K 45/06 | (2006.01) | |
| A61K 31/405 | (2006.01) | |
| A61K 31/4439 | (2006.01) | |

(52) U.S. Cl.
CPC ............ *A61K 31/726* (2013.01); *A61K 45/06* (2013.01); *A61P 3/04* (2018.01); *A61P 3/10* (2018.01); *A61K 31/405* (2013.01); *A61K 31/4439* (2013.01); *A61K 2300/00* (2013.01)

(58) Field of Classification Search
CPC ................ A61K 31/726; A61K 31/405; A61K 2300/00; A61P 3/04; A61P 3/10
USPC .......................................................... 514/54
See application file for complete search history.

(56) References Cited

U.S. PATENT DOCUMENTS

| | | | |
|---|---|---|---|
| 6,166,192 A | 12/2000 | Spiegelman et al. | |
| 7,816,547 B2 * | 10/2010 | Msika ...................... | A23D 9/00 554/12 |
| 2010/0086495 A1 * | 4/2010 | Rubinstein ............. | A61K 9/006 424/48 |
| 2011/0059051 A1 | 3/2011 | Spiegelman et al. | |
| 2011/0104133 A1 | 5/2011 | Tseng et al. | |

FOREIGN PATENT DOCUMENTS

| | | |
|---|---|---|
| CN | 101884643 | 11/2010 |
| JP | 2012135261 | 7/2012 |
| WO | 00/27401 | 5/2000 |
| WO | 2005/067943 | 7/2005 |
| WO | 2010/080985 | 7/2010 |
| WO | 2013/003595 | 1/2013 |
| WO | 2013/137826 | 9/2013 |
| WO | 2017/105229 | 6/2017 |

OTHER PUBLICATIONS

Handbook of Nutraceuticals and Functional Foods, Second Edition, edited by Robert Wildman, CRC Press Taylor & Francis Group, 2007, (562 pages). ISBN 0-8493-6409-4 (Year: 2007).*

Pelletier et al. Treatment With Chondroitin Sulfate Reduces Cartilage Volume Loss in Knee OA Patients Assessed by MRI: A Randomized, Double-Blind, Placebo Controlled Pilot Study. Osteoarthritis and Cartilage 18, Supplement 2 (2010) S143-S144 (Abstract only). (Year: 2010).*

Condrosan, Data Sheet. Capsules: Feb. 4, 2002/Nov. 30, 2006; Envelopes: Feb. 4, 2002. Translated from: https://www.bioiberica.com/es/file/1020/download?token=6o30uLmo (Year: 2002).*

Barbatelli, G. , et al., "The emergence of cold-induced brown adipocytes in mouse white fat depots is determined predominantly by white to brown adipocyte transdifferentiation", Am J Physiol Endocrinol Metab, vol. 298, 2010, E1244-E1253.

Bartelt, Alexander , et al., "Effects of adipocyte lioprotein lipase on de novo lipogenesis and white adipose tissue browning", Biochimica et Biophysica Acta—Molecular and Cell Biology of Lipids, vol. 1831, No. 5, 2013, 934-942.

Cannon, Barbara , et al., "Brown Adipose Tissue: Function and Physiological Significance", Physiol Rev, vol. 84, 2004, 277-359.

Carmona, M. Carmen, et al., "Mitochondrial Biogenesis and Thyroid Status Maturation in Brown Fat Require CCAAT/Enhancer-binding Protein alpha", The Journal of Biological Chemistry, vol. 277, No. 24, 2002, 21489-21498.

Cawthorn, William P., "Wnt6, Wnt10a and Wnt10b inhibit adipogenesis and stimulate osteoblastogenesis through a β-catenin-dependent mechanism", Bone, vol. 50, 2012, 477-489.

Christiaens, Valerie , et al., "CD36 promotes adipocyte differentiation and adipogenesis", Biochimica et Biophysica—General Subjects, vol. 1820, No. 7, 2012, 949-956.

Cristancho, Ana G., et al., "Forming functional fat: a growing understanding of adipocyte differentiation", Nature Reviews Molecular Cell Biology, vol. 12, 2011, 722-734.

Farmer, Stephen R., "Transcriptional control of adipocyte formation", Cell Metabolism, vol. 4, 2006, 263-273.

(Continued)

*Primary Examiner* — Yih-Horng Shiao
(74) *Attorney, Agent, or Firm* — Peacock Law P.C.; Janeen Vilven (57) ABSTRACT

The invention relates to a pharmaceutical composition, comprising (i) a compound comprising at least one carbohydrate and containing at least one sulphate, in combination with (ii) at least one non-protein or non-NA-strand compound, different from (i), that can activate PPAR, preferably PPARγ, and (iii) optionally, at least one pharmaceutically acceptable carrier. Preferably, the sulphated compounds include single sulphur containing agents like MSM or multiple sulphur containing agents like pentosan, Adequan®. The second part of the composition, is a PPARγ agonists chosen from the group of thiazolidinediones, NSAIDs, sulphonylureas and indoles, like for example indomethacin or pioglitazone.

19 Claims, 3 Drawing Sheets

(56) References Cited

OTHER PUBLICATIONS

Fisher, Ffolliott M., et al., "FGF21 regulates PGC-1α and browning of white adipose tissues in adaptive thermogenesis", Genes & Development, vol. 26, 2012, 271-281.
Ghosh, Peter, et al., "Pentosan polysulfate promotes proliferation and chondrogenic differentiation of adult human bone marrow-derived mesenchymal precursor cells", Arthritis Research & Therapy, vol. 12, R28, 2010, 1-17.
Giralt, M., "White, brown, beige/brite: different adipose cells for different functions", Endocrinology, Bol. 154, No. 9, 2013, 2992-3000.
Himms-Hagen, Jean, "Brown adipose tissue thermogenesis and obesity", Progress in Lipid Research, vol. 28, No. 2, 1989, 67-115.
Himms-Hagen, Jean, "Brown adipose tissue thermogenesis: interdisciplinary studies", The FASEB Journal, vol. 4, No. 11, 1990, 2890-2898.
Ichimura, Atsuhiko, et al., "Dysfunction of lipid sensor GPR120 leads to obesity in both mouse and human", Nature, vol. 483, 2012, 350-354.
Jin, T., "The WNT signalling pathway and diabetes mellitus", Diabetolgia, vol. 51, 2008, 1771-1780.
Kennell, Jennifer A., et al., "Wnt Signaling Inhibits Adipogenesis through β-Catenin-dependent and -independent Mechanisms", The Journal of Biological Chemistry, vol. 280, No. 25, 2005, 24004-24010.
Kumagai, Kenji, et al., "Sodium pentosan polysulfate resulted in cartilage improvement in knee osteoarthritis—An open clinical trial", BMC Clinical Pharmacology, vol. 10, No. 7, 2010, 1-9.
Li, Xiaofeng, et al., "Chemical and genetic evidence for the involvement of Wnt antagonist Dickkopf2 in regulation of glucose metabolism", PNAS, vol. 109, No. 28, 2012, 11402-11407.
Linhart, Heinz G., et al., "CyEBPalpha is required for differentiation of white, but not brown, adipose tissue", PNAS, vol. 98, No. 22, 2001, 12532-12537.
Nishina, Patsy M., et al., "Atherosclerosis in genetically obese mice: The mutants obese, diabetes, fat, tubby, and lethat yellow", Metabolism, vol. 43, No. 5, 1994, 554-558.
Nolte, Robert T., et al., "Ligand binding and co-activator assembly of the peroxisome proliferator-activated receptor-γ", Nature, vol. 395, 1998, 137-143.
Orava, Janne, et al., "Different Metabolic Responses of Human Brown Adipose Tissue to Activation by Cold and Insulin", Cell Metabolism, vol. 14, 2011, 272-279.
Palsgaard, Jane, "Cross-talk between Insulin and Wnt Signaling in Preadipocyts", The Journal of Biological Chemistry, vol. 287, No. 15, 2012, 12016-12026.
Petrovic, Natasa, et al., "Chronic Peroxisome Proliferator-activated Receptor γ (PPARγ) Activation of Epididymally Derived White Adipocyte Cultures Reveals a Population of Thermogenically Competent, UCP1-containing Adipocytes Molecularly Distinct from Classic Brown Adipocytes", The Journal of Biological Chemistry, vol. 285, No. 10, 2010, 7153-7164.
Rosenwald, Matthias, et al., "Bi-directional interconversion of brite and white adipocytes", Nature Cell Biology, vol. 15, 2013, 659-667.
Sampath, Harini, et al., "The role of stearoyl-CoA desaturase in obesity, insulin resistance, and inflammation", Ann. N.Y. Acad. Sci., vol. 1243, 2011, 47-53.
Sawada, Takashi, et al., "Perilipin Overexpression in White Adipose Tissue Induces a Brown Fat-Like Phenotype", PNOS, vol. 5, No. 11, e14006, 2010, 1-9.
Sawant, Anandi, et al., "Noggin is Novel Inducer of Mesenchymal Stem Cell Adipogenesis", The Journal of Biology Chemistry, vol. 287, No. 15, 2012, 12241-12249.
Schuchman, Edward H., et al., "Pentosan Polysulfate: A Novel Therapy for the Mucoploysaccharidoses", PLOS ONE, vol. 8, No. 1, e54459, 2013, 1-13.
Seale, Patrick, et al., "PRDM16 controls a brown fat/skeletal muscle switch", Nature, vol. 454, 2008, 961-967.
Sears, Irinia B., et al., "Differentiation-Dependent Expression of the Brown Adipocyte Uncoupling Protein Gene: Regulation by Peroxisome Proliferator-Activated Receptor-γ", Molecular and Cellular Biology, vol. 16, No. 7, 1996, 3410-3419.
Shan, Tizhong, et al., "Fatty acid binding protein 4 expression marks a population of adipocyte progenitors in white and brown adipose tissues", The FASEB J., vol. 27, 2013, 277-287.
Shehzad, A., et al., "Adiponectin: regulation of its production and its role in human diseases", Hormones (Athens), vol. 11, No. 1, 2012, 8-20.
Shen, Longxiang, et al., "Inhibition of adipocytogenesis by canonical WNT signaling in human mesenchymal stem cells", Experimental Cell Research, vol. 317, 2011, 1796-1803.
Souza, Sandra C., et al., "Perilipin regulates the thermogenic actions of norepinephrine in brown adipose tissue", Journal of Lipid Research, vol. 48, 2007, 1273-1279.
Spiegelman, Bruce M., et al., "Adipogenesis and Obesity: Rounding Out the Big Picture", Cell, vol. 87, 1996, 377-389.
Suzuki, Daisuke, et al., "Changes in Ucp1, D2 (Dio2) and Glut4 (S1c2a4) mRNA Expression in Response to Short-Term Cold Exposure in the House Musk Shrew (*Suncus murinus*)", Exp. Anim., vol. 56, No. 4, 2007, 279-288.
Wu, Jun, et al., "Beige Adipocytes Are a Distinct Type of Thermogenic Fat Cell in Mouse and Human", Cell, vol. 150, 2012, 366-376.
Wu, Jin, et al., "Inhibition of inflammation by pentosan polysulfate impedes the development and progression of severe diabetic nephropathy in aging C57B6 mice", Laboratory Investigation, vol. 91, 2011, 1459-1471.
Xu, H. Eric, et al., "Structural determinants of ligand binding selectivity between the peroxisome proliferator-activated receptors", PNAS, vol. 98, No. 24, 2001, 13919-13924.
Zhou, Zhihong, et al., "Cidea-deficient mice have lean phenotype and are resistant to obesity", Nature Genetics, vol. 35, 2003, 49-56.
Zhu, Yijun, et al., "Structural organization of mouse peroxisome proliferator-activated receptor γ (mPPARγ) gene: Alternative promoter use and different splicing yield two mPPARγ isoforms", Proc. Natl. Acad. Sci USA, vol. 92, 1995, 7921-7925.

* cited by examiner

COMPOSITIONS AND METHODS FOR INDUCING BEIGE OR BROWN FAT TISSUE

CROSS-REFERENCE TO RELATED APPLICATIONS

This application is a continuation of International Application PCT/NL2016/050871, entitled "Compositions and Methods for Inducing Beige or Brown Fat Tissue", filed on Dec. 14, 2016, which claims priority to Netherlands Patent Application No. 2015957, filed Dec. 14, 2015, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COM-PACT DISC

Not Applicable.

COPYRIGHTED MATERIAL

Not Applicable.

FIELD OF THE INVENTION

The invention relates to a compositions and methods for inducing beige or brown fat tissue, and for uses thereof in e.g. the treatment of obesity, diabetes-II and other weight related disorders.

BACKGROUND OF THE INVENTION

Obesity is a growing health problem in the Western world and is characterized by an inappropriate expansion of fat cells. Obesity affects an estimated number of 30-50% of the middle aged population in the Western world. Obesity is defined as a body mass index (BMI) of 30 m/kg$^2$ or more, and contributes to diseases such as coronary artery disease, hypertension, stroke, diabetes, hyperlipidemia and some cancers (see e.g. Nishina, P. M. et al. (1994), Metab. 43:554-558; Grundy, S. M. & Barnett, J. P. (1990), Diss Mon 36:641-731).

Generally, obesity results when energy intake exceeds energy expenditure, resulting in the growth and/or formation of adipose tissue via hypertropic and hyperplastic growth. Hypertropic growth is an increase in size of adipocytes stimulated by lipid accumulation. Hyperplastic growth is defined as an increase in the number of adipocytes in adipose tissue. It is thought to occur primarily by mitosis of pre-existing adipocytes caused when adipocytes fill with lipid and reach a critical size. An increase in the number of adipocytes has far-reaching consequences for the treatment and prevention of obesity.

Adipose tissue can be distinguished in 2 main types of tissue: brown (BAT) and white (WAT) adipose tissue. Five percent of the body mass in newborns is BAT, which then diminishes with age. BAT is located mainly in the neck, along the upper half of the spine and toward the shoulders as well surrounding the great vessels in the abdomen and around the kidneys. WAT stores and releases fat according to the nutritional needs of the animal. This stored fat is used in the body for heat insulation (e.g. subcutaneous fat), mechanical cushion (e.g. surrounding internal organs) and as a source of energy.

BAT on the other hand generates body heat by burning fat. BAT contains a high number of mitochondria that express the specific brown fat marker uncoupling protein-1 (UCP1). Brown adipocytes contain, in contrast to white adipocytes, numerous smaller lipid droplets and their nuclei are almost centrally located. In adults BAT is still present around vital organs, in the neck and along back and sternum.

It is thought, that by burning the excess energy, stored in lipid, BAT can counteract obesity and diabetes. Therefore, several authors have suggested to insert brown fat cells into adipose tissue, to induce BAT in human. Exemplary disclosures include WO2010/080985, WO2013/003595, US2011/104133, US2011/059051 and U.S. Pat. No. 6,166,192.

It is now clear that there are two distinct types of brown adipose cells, see Fisher F. M. et al. Genes Dev. 26: 271-281 (2012). Classical brown fat derived from a myf-5 positive cellular lineage and UCP1-positive cells that emerge in white fat from a myf-5 negative lineage.

Wu J. et al. Cell 150, 366-376 (2012) report the isolation of "beige" cells from murine white fat depots. Beige cells resemble white fat cells in having extremely low basal expression of UCP1, but, like classical brown fat, they respond to cyclic AMP stimulation with high UCP1 expression and turn on a robust program of respiration and energy expenditure that is equivalent to that of classical brown fat cells. Beige cells have a gene expression pattern distinct from either white or brown fat and are preferentially sensitive to the polypeptide hormone irisin, a polypeptide hormone secreted by muscle and increased with exercise. Finally, they provide evidence that previously identified brown fat deposits in adult humans are composed of beige adipocytes. Beige adipose tissue is also denoted as "brite adipose tissue", and often beige/brite is used together.

In addition, UCP1-positive, brown fat-like cells can emerge in most white fat depots upon prolonged cold exposure or β3-adrenergic receptor activation, see Barbatelli G. et al., Am J. Physiol. Endocrinol. Metab. 298, E1244-E1253 (2010).

β1-Adrenoceptor controls brown pre-adipocyte density, and β3-adrenoceptor controls white to brown adipocyte transdifferentiation. Barbatelli G. et al. report a central role for β3-adrenoceptor in cold emergence of brown adipocytes in "white" fat depots. While the expression of PGC-1α, C/EBPβ, PRDM16, Cidea and COX8b mRNA displayed a similar pattern, Garcia-Alonso V et al., J. Biol. Chem.aug (2013) demonstrate PGE2 as a key regulator of white-to-brown adipogenesis.

Fisher F. M. et al. Genes Dev. 26: 271-281 (2012) report that FGF21 can increase thermogenic gene expression, such as UCP1 and CIDEA, in BAT and primary classical brown adipocytes. However, they found that FGF21 had far more profound effects on thermogenic gene expression in specific WAT depots. They wrote that FGF21 is thus far the only known cold-induced secreted protein that functions to increase the appearance of brown-like/beige adipocytes in WAT depots. PGC-1α has been recognized as a critical regulator of thermogenesis and oxidative metabolism. It is therefore not completely surprising that this co activator of transcription is important to the thermogenic effects of FGF21 both in culture and in vivo.

Li X. PNAS. Vol. 109, no. 28, 11402-11407 (2012) showed (in in vivo experiments) that Dickkopf related protein (DKK2) deficiency was associated with increased hepatic glycogen accumulation and decreased hepatic glucose output. DKK2 deficiency did not cause an increase in insulin production but resulted in increased Wnt activity and glucagon-like peptide 1 (GLP1) production in the intestines. Given together that DKK2 inhibitors reduced blood-glucose concentrations and improved glucose tolerance in a murine model of type 2 diabetes (db/db), Li X. suggest that DKK2 may be a potential therapeutic target for treating type 2 diabetes.

Jin T. Diabetologia 51, 1771-1780 (2008) report that the Wnt pathway is involved in lipid metabolism and glucose homeostasis, and mutations in LRP5 may lead to the development of diabetes and obesity. The Wnt co-receptor LRP5 is essential for normal lipid metabolism and glucose-induced insulin secretion while polymorphisms in Wnt5B have been shown to be associated with the risk of type 2 diabetes.

It has been demonstrated that LRP5 can interact with axin, one of the inhibitors of the Wnt pathway. Reduced Wnt activity is important for lipid and glucose metabolism, pancreatic beta cell proliferation and function, and the production of the incretin hormone GLP1.1.

Figure 1:
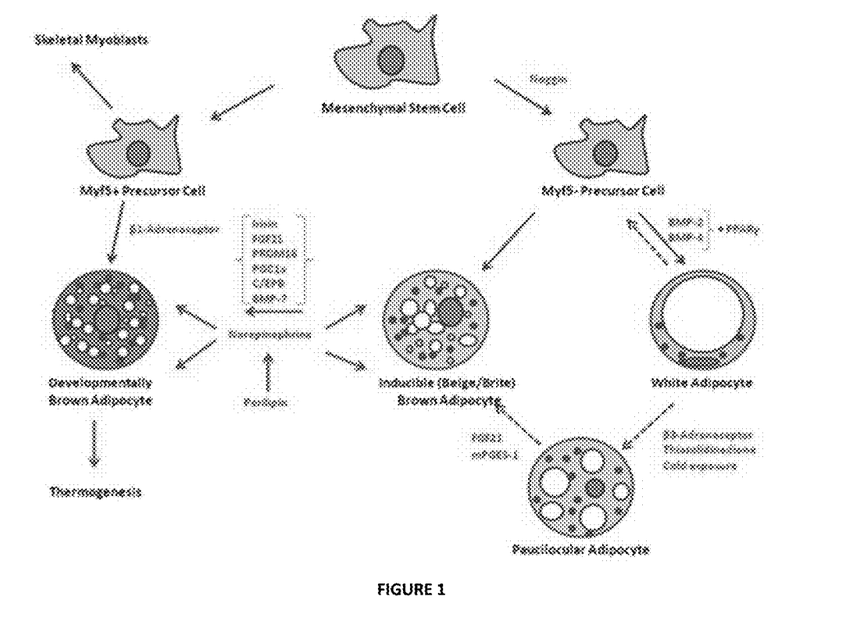
FIG. 1 shows schematically the major determination pathways; see: Giralt M. and Villarroya F. Endocrinology 2013 as doi:10.1210/en.2013-1403.

FIG. 1 shows schematically the major determination pathways in adipocyte differentiation; see: Giralt M. and Villarroya F. Endocrinology 2013 as doi:10.1210/en.2013-1403.

FIG. 1 shows that BAT and WAT cells are thought to arise from mesenchymal stem (progenitor) cells (MSC). First, so called pre-adipocytes are formed, which can differentiate to either white, beige/brite or brown adipose tissue. BAT and WAT tissue express a number of genes differently, and by now a substantial number of genes is known to be indicative for BAT or WAT tissue. One of the major genes involved in the expression of BAT is the expression of uncoupling protein-1 (UCP-1). An increased level of transcription of the UCP-1 gene is a critical component in the cascade of events, leading to elevated BAT thermogenesis in response to an increase in beta-adrenergic stimulation followed by an increase in cAMP levels.

PPARγ, a nuclear hormone receptor (Zhu, Y. et al. (1995) PNAS 92:7021-7925) functions as a major regulator for fat-specific genes, and for an entire program of adipogenesis (Spiegelman, B. M. and Flier J. S. (1996) Cell 87:377-389). PPAR-γ mediates ligand-dependent transcription and is activated, beside by the synthetic agonists thiazolidinediones (TZDs), by naturally occurring compounds, such as long chain fatty acids and the prostaglandin 15-deoxy Δ, prostaglandin J2 (15d-PGJ2), but also nonsteroidal anti-inflammatory drugs (NSAIDs), as ibuprofen, fenoprofen, and indomethacin.

The two key transcription factors during adipocytes differentiation are found to be CCAAT/enhancer binding protein alpha and delta (C/EBPα/C/EBPδ) and peroxisome proliferator-activated receptor γ (PPARγ); see Farmer S. R.; Cell Metabolism 4, 263-273 (2006). PPARγ and C/EBPα cross-regulate each other and they are both necessary for the development of all types of adipose cells. However, the absence of C/EBPa in mice prevents the development of white, but not brown, adipose depots, indicating that lack of C/EBPa can be compensated in brown fat development probably via the C/EBPβ signaling pathway: Linhart H G et al. Proc Natl Acad Sci USA. 98, 12532-12537 (2001) and Carmona M C et al. J BiolChem., 277:21489-21498 (2002).

Sawant A. et al. The Journal of Biological Chemistry 287, No. 15, 12241-12249 (2012) report a novel mechanism by which noggin (a polypeptide that binds and inactivates members of the transforming growth factor-beta (TGF-beta) superfamily signaling proteins, such as bone morphogenetic protein-4) directly induces adipogenesis of mesenchymal stem cells independently of the major human adipogenic signals C/EBPδ, C/EBPα and PPARγ. The results of that study indicate that noggin acts as a key regulator balancing bone formation and adipogenesis. The study identified that noggin-mediated adipogenesis of MSC is independent of known adipogenesis pathways, which involve activation of the signaling pathways of: PI3K, mTOR/Akt, and cAMP. Noggin was able to induce expression of all the three transcription factors (C/EBPδ, C/EBPα and PPARγ) during adipocyte differentiation of MSC. The factors that lead to noggin up-regulation remain unexplored. There are some possible mechanisms that may be considered.

Insulin-like growth factor-1 (IGF-1) is an important differentiation factor for osteoblasts, suppresses noggin expression. A role for the tissue specific transcription factor Pax-1 in adipogenesis is also suggested. Further studies need to explain the molecular mechanism of noggin-induced Pax-1 up-regulation. IGF-1, BMP-2 and BMP-4 are potent inhibitors of Pax-1. Thus, down-regulation of BMP-2 by noggin may also be a mechanism for elevated Pax-1 expression to facilitate adipogenesis.

BAT thermogenesis is used both to maintain homeothermy by increasing thermogenesis in response to lower temperatures and to maintain energy balance by increasing energy expenditure in response to increase in caloric intake (Sears, I. B. et al. (1996) Mol. Cell. Biol. 16(7):3410-3419). Nearly all experimental rodent models of obesity are accompanied by diminished or defective BAT function, usually as the first symptom in the progression of obesity (Himms-Hagen, J. (1989) Prog. Lipid Res. 28:67-115; Himms-Hagen J. (1990) FASEB J. 4:2890-2898). Hence, an increase in BAT is expected to have the effect of increasing thermogenesis, and thereby lowering of body weight.

Incidentally WO 2013/137826 A1 recites methods of generating functional human brown adipocytes, comprising exposing human stem cells, progenitor cells, or white adipocytes to culture with an differentiation cocktail that comprises one or more browning agents (e.g., one or more macromolecular crowders), and optionally one or more adipogenic agents, are described, as are populations of human brown adipocytes generated by the methods, and uses for the populations. JP 2012135261 recites a differentiation-inducing promoter and a differentiation-inducing method, for efficiently and selectively making a differentiation induction from stem cells to brown adipose cells. The differentiation-inducing promoter from stem cells to brown adipose cells is provided, with Gdf (growth differentiation factor) as an active ingredient. The differentiation-inducing method for such brown adipose cells is also provided, including culturing cells in the presence of Gdf. The invention is also applicable to prevention and/or amelioration of diabetes, metabolic syndrome and/or obesity. Petrovic et al. in J. Biol. Chem. Vol 285, No. 10, p. 7153-7164, March 2010, recite a chronic peroxisome proliferator-activated receptor γ (PPARγ) activation of epididymally derived white adipocyte cultures reveals a population of thermogenically competent, UCP1-containing adipocytes molecularly distinct from classic brown adipocytes. WO 2005/067943 A1 recites pharmaceutical compositions comprising of glycosaminoglycan or salts thereof, preferably chondroitin or salts thereof, more preferably chondroitin sulphate, and nonsteroidal anti-inflammatory drug(s) or salts thereof, optionally with pharmaceutically acceptable excipient(s). The compositions provide gastrosparing effect in conditions where nonsteroidal anti-inflammatory drug(s) or their salts are used, particularly in mammals. CN 101 884 643 A recites application of pioglitazone and heparin or low molecular heparin or pharmaceutically acceptable salts thereof or derivatives thereof to preparing a pharmaceutical composition, in particular to the application to preparing a medicament for preventing or treating fatty liver. The purpose of the pioglitazone and the heparin or the low molecular heparin or the pharmaceutically acceptable salts thereof in lessening fat deposition in rat hepatocytes and the synergy of a pioglitazone and heparin or low molecular heparin compound in preventing or treating the rat fatty liver are proved by animal tests. These documents do not relate to obesity related disorders.

The induction of BAT from progenitor cells is described, and generally involves biologics like proteins, DNA-sequences, antibodies or antisense nucleic acid sequences, see WO2010/080985, WO2013/003595, US2011/104133, US2011/059051 and U.S. Pat. No. 6,166,192.

SUMMARY OF THE INVENTION

It is an object of the invention to provide a composition that is able to induce beige/brite and/or brown adipose tissue from progenitor cells. The invention furthermore provides method of use of such composition, and for the treatment of obesity related disorders.

The invention provides for a pharmaceutical composition, comprising a first compound comprising at least one carbohydrate and containing at least one sulphate, and a second compound, different from the first compound, that can activate PPAR, preferably PPARγ.

A compound that can activate PPAR means that the PPAR receptor activity increases by at 2 to 3 times compared to a baseline situation without the PPAR activating compound.

The compound that can activate PPAR is not a protein, or not a nucleic acid (NA)-strand compound. Suitable compounds that can activate PPAR include thiazolidinediones, NSAIDs, sulphonylureas and indoles.

Inventors discovered that stimulation of mesenchymal progenitor cell lines by a compound comprising a carbohydrate comprising at least one sulphate group like Pentosan in combination with a PPAR, preferably a PPARγ agonist, like indomethacin or pioglitazone stimulated synergistically the formation of adipocytes with Beige/Brite and/or BAT characteristics.

Preferably, the stimulation can be observed in the MSC KS483 cell line from Percuros, The Netherlands, deposited at DSMZ, Inhoffenstr. 7B, D-38124 Braunschweig, Germany, in the name of the applicant under accession number DSM ACC3286 on Jan. 13, 2016, but other cell lines of comparable origin can be used as well.

The invention therefore provides a pharmaceutical composition, comprising a compound comprising at least one carbohydrate (saccharide) and containing at least one sulphate, in combination with a second compound that can activate PPAR, preferably PPARγ, for use in the treatment of obesities and other weight related disorders.

The Beige/Brite and Brown adipose tissue have many characteristics in common (see Endocrinology 1403-1411 (2013)) and hereinafter they will be named "BAT", unless specifically mentioned.

Hence, patients with obesity or obesity related disorders such as for example coronary artery disease, atherosclerosis, metabolic syndrome, hypertension, stroke, diabetes, hyperlipidemia and some cancers are expected to benefit from treatment with the pharmaceutical composition of the invention.

Therefore, the invention also relates to the use of the pharmaceutical composition as described as a medicament.

Preferably, the invention further relates to the pharmaceutical composition of the invention, for use in the treatment of obesity related disorders like coronary artery disease, atherosclerosis, metabolic syndrome, hypertension, stroke, diabetes, hyperlipidemia and some cancers.

More in particular, the invention also relates to pharmaceutical composition of the invention for use in the treatment of obesity or diabetes-II.

In another embodiment of the invention, the invention relates to a method for the inducement of beige/brite and/or brown fat tissue in vitro, by administering an effective amount of the pharmaceutical composition of the invention to mesenchymal progenitor cells, for sufficient period, to induce said beige/brite and/or brown fat tissue.

In a further embodiment of the invention, the invention relates to a method for the inducement of beige/brite and/or brown fat tissue in vivo, by administering an effective amount of the pharmaceutical composition of the invention to tissue adipose tissue, for sufficient period, to induce said beige/brite and/or brown fat tissue.

Preferably, the method of inducement of beige/brite and/or brown fat tissue in vivo comprises the administration of the composition of the invention to a pet or mammal comprising said tissue.

More preferably, the mammal is a human, and the treatment most preferably is performed on human having a BMI higher than 30.

The pharmaceutical composition according the invention may be a combination composition, wherein the active pharmaceutical ingredients are in one dosage form. The pharmaceutical composition may also comprise separate dosage forms for individual pharmaceutical active ingredients.

The compound comprising at least one carbohydrate and containing at least one sulphate preferably has anti-inflammatory effects, meaning that at least one of the inflammatory markers is reduced. Inflammatory markers are e.g. TNFα, IFN, cytokines, histamine, interleukines, chemokines, leukotrienes, lysosome granules and prostaglandins.

The compound that activates PPAR, preferably PPARγ preferably is a compound that can activate PPAR, meaning the PPAR receptor activity increases by at least 2-3 times compared to a baseline situation without the PPAR activating compound.

The compound that activates PPAR, preferably PPARγ preferably has anti-inflammatory effects, meaning that at least one of the inflammatory markers is reduced. Inflammatory markers are e.g. TNFα, IFN, cytokines, histamine, interleukines, chemokines, leukotrienes, lysosome granules and prostaglandins.

Preferred compounds that activate PPARγ include thiazolidinediones, NSAIDs, sulphonylureas and indoles, and particularly preferred compounds include indomethacin and pioglitazone.

In a preferred embodiment, the active pharmaceutical ingredients are combined in one dosage form, preferably oral dosage form. With such dosage form, all fat depots in a body are targeted.

In a further preferred embodiment, the combination of above mentioned compounds is formulated in a form, such as for example nanoparticles, that depending on its use will be suitable to be targeted to specific cells, tissues or organs. For example, the nanoparticle may be any kind of nanodevice in which both compounds are packaged for targeted delivery.

In a more preferred embodiment, targeting can be done by any specific molecule attached on the outside of the specific form, such as for example a nanoparticle, like an antibody, or other molecular or chemical entity that can target specific cells, tissues or organs.

The effect of the treatment may be determined by in vitro and/or in vivo assays, determining the formation of brown and/or brite-beige adipose tissue, and/or the change in regulation of relevant genes. Relevant genes are for example described in the following references: In general: Cristancho A. G. and Lazar M. A. Nature rev Mol. Cell Biol. 12, 722-734 (2011), Perilipin: Souza S. C. et al., J. Lipid Res.48: 1273-1279 (2007), Sawada T. et al., PLoS ONE Vol. 5, Issue 11, e14006 (2010).
CD36: Christiaens V. et al., Bioch. et Bioph. Acta 1820, 949-956 (2012),
FABP4: Shan T. et al., The Faseb Journal 27, 277-287 (2013),
LPL: Bartelt A, et al., Biochim Biophys Acta. 1831(5), 934-42 (2013)
Slc2a4 (glut4) and UCP1: Suzuki D. et al., Exp. Anim. 56, (4) 279-288 (2007), Slc2a4 (glut4): Orava J. et al., Cell Metabolism 14, 272-279 (2011),
O3far1 (GPR120): Ichimura A. et al., Nature 483, 350-354 (2012),
Cidea: Zhou Z. et al., Nature Genetics 35 (1), 49-56 (2003), Prdm16: Seale P. et al., Nature Vol. 454, 961-968 (2008)
Adiponectin: Shehzad A. et al., Hormones, 11(1):8-20 (2012)
Wnt and Adipsin: Shen L. et al., Experimental cell research 317 1796-1803 (2011)
Scd1: Sampath H, et al., Ann. N.Y. Acad. Sci. 1243 47-53 (2011).

DETAILED DESCRIPTION OF THE INVENTION

The invention provides for a pharmaceutical composition, comprising (i) at least one compound comprising a carbohydrate (saccharide) and containing at least one sulphate, in combination with (ii) at least one non-protein or non-NA-strand compound, different from compound (i), that can activate PPAR, preferably PPARγ, and (iii) optionally, at least one pharmaceutically acceptable carrier.

A carbohydrate is an organic compound comprising only carbon, hydrogen, and oxygen, usually with a hydrogen: oxygen atom ratio of 2:1 (as in water); with the empirical formula $C_m(H_2O)_n$ (where m could be different from n). Structurally it is more accurate to view carbohydrates as polyhydroxy aldehydes and ketones.

The term is most common in biochemistry, where it is a synonym of saccharide. The carbohydrates (saccharides) are divided into four chemical groupings: monosaccharides, disaccharides, oligosaccharides, and polysaccharides. In general, the monosaccharides and disaccharides, which are smaller carbohydrates, are commonly referred to as sugars. In the description, "carbohydrate" means mono-, di-, oligo- or polysaccharides, unless specifically mentioned.

Carbohydrates perform numerous roles in living organisms. Polysaccharides serve for the storage of energy (e.g., starch and glycogen), and as structural components (e.g., cellulose in plants and chitin in arthropods). The 5-carbon monosaccharide ribose is an important component of coenzymes (e.g., ATP, FAD, and NAD) and the backbone of the genetic molecule known as RNA. The related deoxyribose is a component of DNA. Saccharides and their derivatives include many other important biomolecules that play key roles in the immune system, fertilization, preventing pathogenesis, blood clotting, and development.

Carbohydrates as used in the present invention do not relate to glycosylated proteins or nucleoside compounds (like DNA, RNA or the like).

The carbohydrate preferably is a Glycosaminoglycans (GAGs) or keratan. Glycosaminoglycans, or mucopolysaccharides are long unbranched polysaccharides consisting of a repeating disaccharide unit. The repeating unit consists of an amino sugar (N-acetylglucosamine or N-acetylgalactosamine) along with a uronic sugar (glucuronic acid or iduronic acid) or galactose.

Glycosaminoglycans have high degrees of heterogeneity with regards to molecular weight, disaccharide construction, and sulfation due to the fact that GAG synthesis, unlike proteins or nucleic acids, is not template driven, and dynamically modulated by processing enzymes.

Based on core disaccharide structures, GAGS are classified into four groups.
1) Heparin/heparan sulfate (HSGAGs) and
2) chondroitin/dermatan sulfate (CSGAGs) are synthesized in the golgi apparatus, where protein cores made in the rough endoplasmic reticulum are posttranslationally modified with O-linked glycosylations by glycosyltransferases forming a proteoglycan.
3) Keratan sulfate may modify core proteins through N-linked glycosylation or O-linked glycosylation of the proteoglycan.
4) The fourth class of GAG, hyaluronic acid, is not synthesized by the golgi, but rather by integral membrane synthases which immediately secrete the dynamically elongated disaccharide chain.

Chondroitin sulfate and dermatan sulfate (group 2), which comprise CSGAGs, are differentiated from each other by the presence of GlcA and IdoA epimers respectively. Three sulfation events of the CSGAG chains occur: 4-O and/or 6-O sulfation of GalNAc and 2-O sulfation of uronic acid. Four isoforms of the 4-O GalNAc sulfotransferases (C4ST-1, C4ST-2, C4ST-3, and D4ST-1) and three isoforms of the GalNAc 6-O sulfotransferases (C6ST, C6ST-2, and GalNAc4S-6ST) are responsible for the sulfation of GalNAc.

In the third class of GAGs, keratan sulfate elongation begins at the nonreducing ends of three linkage oligosaccharides, which define the three classes of keratan sulfate. Keratan sulfate I (KSI) is N-linked via a high mannose type precursor oligosaccharide. Keratan sulfate II (KSII) and keratan sulfate III (KSIII) are O-linked, with KSII linkages identical to that of mucin core structure, and KSIII linked to a 2-O mannose. Sulfation of the polymer occurs at the 6-position of both sugar residues.

The fourth class of GAG is hyaluronic acid. HA is a linear polysaccharide composed of repeating disaccharide units of →4)GlcAβ(1→3)GlcNAcβ(1→ and has a very high molecular mass, ranging from 105 to 107 kDa.

GAGs Function

Endogenous heparin is localized and stored in secretory granules of mast cells. Histamine that is present within the granules is protonated (H2A2+) at pH within granules (5.2-6.0), thus it is believed that heparin, which is highly negatively charged, functions to electrostatically retain and store histamine. In the clinic, heparin is administered as an anticoagulant and is also the first line choice for thromboembolic diseases. Heparan sulfate (HS) has numerous biological activities and functions, including cell adhesion, regulation of cell growth and proliferation, developmental processes, cell surface binding of lipoprotein lipase and other proteins, angiogenesis, viral invasion, and tumor metastasis.

CSGAGs (group 2 GAGs) interact with heparin binding proteins, specifically dermatan sulfate interactions with fibroblast growth factor FGF-2 and FGF-7 have been implicated in cellular proliferation and wound repair while interactions with hepatic growth factor/scatter factor (HGF/SF) activate the HGF/SF signaling pathway (c-Met) through its receptor. Other biological functions for which CSGAGs are known to play critical functions in include inhibition of axonal growth and regeneration in CNS development, roles in brain development, neuritogenic activity, and pathogen infection.

One of the main functions of the third class of GAGs, keratan sulfates, is the maintenance of tissue hydration. Within the normal cornea, dermatan sulfate is fully hydrated whereas keratan sulfate is only partially hydrated suggesting that keratan sulfate may behave as a dynamically controlled buffer for hydration. In disease states such as macular corneal dystrophy, in which GAGs levels such as KS are altered, loss of hydration within the corneal stroma is believed to be the cause of corneal haze, thus supporting the long held hypothesis that corneal transparency is a dependent on proper levels of keratan sulfate. Keratan sulfate GAGs are found in many other tissues besides the cornea, where they are known to regulate macrophage adhesion, form barriers to neurite growth, regulate embryo implantation in the endometrial uterine lining during menstrual cycles, and affect the motility of corneal endothelial cells. In summary, KS plays an anti-adhesive role, which suggests very important functions of KS in cell motility and attachment as well as other potential biological processes.

Hyaluronic acid, the fourth GAGs group, is a major component of synovial tissues and fluid, as well as other soft tissues, and endows their environments with remarkable rheological properties. For example, solutions of hyaluronic acid are known to be viscoelastic, and viscosity changes with sheer stress. At low sheer stress, a solution of 10 g/L of hyaluronic acid may have a viscosity 106 times the viscosity of the solvent, while under high sheer stress, viscosity may drop by as much as 103 times. The aforementioned rheological properties of solutions of hyaluronic acid make it ideal for lubricating joints and surfaces that move along each other, such as cartilage. In vivo, hyaluronic acid forms hydrated coils that form randomly kinked coils that entangle to form a network. Hyaluronan networks retard diffusion and form a diffusion barrier that regulates transport of substances through intercellular spaces. For example, hyaluronan takes part in the partitioning of plasma proteins between vascular and extravascular spaces, and it is this excluded volume phenomenon that affects solubility of macromolecules in the interstitium, changes chemical equilibria, and stabilizes the structure of collagen fibers. Other functions include matrix interactions with hyaluronan binding proteins such as hyaluronectin, glial hyaluronan binding protein, brain enriched hyaluronan binding protein, collagen VI, TSG-6, and inter-alpha-trypsin inhibitor. Cell surface interactions involving hyaluronan are its well-known coupling with CD44, which may be related to tumor progression, and also with RHAMM (Hyaluronan-mediated motility receptor), which has been implicated in developmental processes, tumor metastasis, and pathological reparative processes. Fibroblasts, mesothelial cells, and certain types of stem cells surround themselves in a pericellular "coat", part of which is constructed from hyaluronan, in order to shield themselves from bacteria, red blood cells, or other matrix molecules. For example, with regards to stem cells, hyaluronan, along with chondroitin sulfate, helps to form the stem cell niche. Stem cells are protected from the effects of growth factors by a shield of hyaluronan and minimally sulfated chondroitin sulfate. During progenitor division, the daughter cell moves outside of this pericellular shield where it can then be influenced by growth factors to differentiate even further.

Preferred types of sulphated saccharides are also known as heparine, heparan sulphate analogues, or heparine-like compounds.

Heparan sulfate analogues, able to interact with CSGAGs (group 2 GAGs) are polymers engineered to mimic several properties of heparan sulfates. They can be constituted with a backbone of polysaccharides, such as poly glucose or glucuronates or a polyester such as co-polymers of lactic or malic acid to which sulfates, sulfonate or carboxylgroups are added in controlled amounts and location. They have a molecular weight that can range from a few thousands to several hundred thousand Dalton. Heparan sulfates can sequester growth factors (GFs) and cytokines in the extracellular matrix (ECM) thereby protecting them from degradation. This ensures local presence of these signaling proteins to fulfill their function in the ECM which contributes to the preservation of anatomical form and function. Heparan sulfates bind to matrix proteins on specific sites called "heparan sulfate binding sites" on ECM macromolecules like collagen, fibronectin and laminin, to form a scaffold surrounding the cells and to protect ECM proteins and growth factors from proteolytic degradation by steric hindrance. However, at any site of inflammation, so also in wound areas, heparan sulfates are degraded, mainly by heparanases giving free access to protease to degrade the ECM and a subsequent loss of GFs and cytokines that disrupts the normal tissue homeostasis.

Heparan sulfate analogues obtain many of the characteristics of heparan sulfates including the ability to sequester GFs and bind and protect matrix proteins. However, heparan sulfate analogues are resistant to enzymatic degradation. This way they strengthen the healing potential of the wound bed by repositioning GFs and cytokines back into the ECM.

Several heparan sulfate analogues (also known as ReGeneraTing Agents, RGTA) have been developed from a poly glucose backbone. Heparan sulfate analogues will occupy the free heparan sulfate binding sites on ECM macromolecules like collagen, fibronectin and laminin that become available following heparan sulfate degradation. In many characteristics heparan sulfate analogues are similar to the natural heparan sulfate. The most important difference is their resistance to enzymatic degradation. The resistance of RGTA is caused by the coupling of the subunits internal bond of the molecules. The β2-4 carbon-carbon binding of the subunits of heparan sulfate is prone to enzymatic cleavage whereas the α1-6 carbon-carbon binding of the subunits of heparan sulfate analogues are resistant to cleavage by all known mammalian glycanases and heparanases. This way RGTA can recreate a scaffold with the ECM proteins and will reposition GFs back into the matrix where they can re-unfold their natural action in wound repair.

Suitable compounds comprising a carbohydrate and a sulphate group can be derived from natural sources, or can be made—at least in part—synthetically.

Examples of sulphated compounds include single sulphur containing agents like MSM (dimethylsulfon), dextrane sulphate, or multiple sulphur containing agents, like polysulphated glycosaminoglycan (Adequan®), heparine like pentosan or the like.

Preferred sulphated saccharides compounds are polysulphated glycosaminoglycan (Adequan), heparine like pentosan polysulfate (Elmiron) or the like.

The second part of the present composition, is an agent that can activate PPAR, preferably PPARγ. Preferred PPAR agonists include triglitazones (TZDs: triglitazone, rosiglitazone, pioglitazone etc.) and indomethacin.

PPARγ mediates ligand-dependent transcription and is activated, beside synthetic agonists TZDs, by naturally occurring compounds, such as long chain fatty acids and the prostaglandin 15-deoxy Δ, prostaglandin J2 (15d-PGJ2), but also few nonsteroidal anti-inflammatory drugs (NSAIDs), as ibuprofen, fenoprofen, and indomethacin. PPAR agonists bind in distinct manner to the ligand-binding pocket of the PPARγ receptor leading to differential cofactor displacement and recruitment to the receptor, ultimately resulting in tissue and promoter-selective gene expression. Full PPARγ agonists share a common binding mode, in which acidic head groups bind with amino acid residues Y437, H449, Y314 and H323 within the ligand-binding pocket of PPARγ. These interactions stabilize a charge clamp between the C-terminal activation function 2 (AF-2) helix and a conserved lysine residue on the surface of the receptor, through which coactivator proteins are recruited to the receptor (Nolte R et al, Nature, 1998, Xu E et al, PNAS 2001).

Preferably, both the compound comprising at least one carbohydrate and containing at least one sulphate and the compound that activates PPARγ preferably has anti-inflammatory effects, meaning that at least one of the inflammatory markers is reduced. Inflammatory markers are e.g. TNFα, IFN, cytokines, histamine, interleukines, chemokines, leukotriene, lysosome granules and prostaglandins.

Whether a compound is a PPAR, preferably PPARγ agonist can be determined in a simple cell-based test:

To test PPAR activating potential of a compound, KS-483 cells are transfected with firefly and Renilla luciferase vectors.

Luciferase assay was performed according to the protocol of the dual-luciferase reporter assay system (Promega). Following the manufacturer's protocol cells were transiently transfected with PPAR Luc (PPRE Luc) to determine the expression of PPAR and co-transfected with Renilla luciferase construct to correct for transfection efficiency.

The PPAR reporter is a mixture of a PPAR-responsive firefly luciferase construct (PPRE Luc) and a constitutively expressing Renilla element.

Firefly and Renilla luciferases, because of their distinct evolutionary origins, have dissimilar enzyme structures and substrate requirements. These differences make it possible to selectively discriminate between their respective bioluminescent reactions.

Firefly luciferase is a 61 kDa monomeric protein that does not require posttranslational processing for enzymatic activity. Thus, it functions as a genetic reporter immediately upon translation in a cell. Photon emission is achieved through oxidation of beetle luciferin in a reaction that requires ATP, $Mg^{2+}$ and $O_2$. Under conventional reaction conditions, the oxidation occurs through a luciferyl-AMP intermediate that turns over very slowly. As a result, this assay chemistry generates a "flash" of light that rapidly decays after the substrate and enzyme are mixed.

Renilla luciferase, a 36 kDa monomeric protein, is composed of 3% carbohydrate when purified from its natural source, Renilla reniformis. However, like firefly luciferase, post-translational modification is not required for its activity, and the enzyme may function as a genetic reporter immediately following translation. The luminescent reaction catalyzed by Renilla luciferase utilizes oxygen and coelenterate-luciferin. the kinetics of the Renilla luciferase reaction provide a stabilized luminescent signal that decays slowly over the course of the measurement. Similar to firefly luciferase, the luminescent reaction catalyzed by Renilla luciferase also provides extreme sensitivity and a linear range generally extending six orders of magnitude.

Twenty hours after transfection of the KS-483 cells, cells were washed with phosphate buffered saline (PBS) and subsequently stimulated with a compound or compound mixture in α-MEM medium supplemented with 10% heat-inactivated fetal calf serum (FCS). After stimulation cells were washed again in PBS, lysed and luciferase activity was determined by measurement of luminescence. PPAR activating potential on the Firefly luciferase is shown in relative luciferase units compared to the constitutive Renilla luciferase.

By PPAR agonist is meant any compound that increases the biological activity or expression of one or more PPARs (e.g., PPARα, PPARγ, and PPARβ/δ) in a cell by a least 10% relative, preferably at least 2-3 times.

Examples of PPARγ agonists include any of the Thiazolidinediones, but particularly Rosiglitazone, Troglitazone and Pioglitazone and analogs thereof. Rosiglitazone is the preferred PPAR agonist. Additional examples of PPARγ agonists include non-steroidal anti-inflammatory drugs, such as Indomethacin, Ibuprofen, Naprosyn and Fenoprofen and antioxidants such as vitamin E, vitamin C, S-adenosyl methionine, selenium, beta-carotene, idebenone, cysteine, dithioerythritol, dithionite, dithiothreitol, and pyrosulfite.

Examples of PPARα agonists include any of the fibrates (e.g., fenofibrate, bezafibrate, gemfibrozil, and analogs thereof), docosahexaenoic acid, and Wy 4643.

So for example Pentosan in combination with one of these compounds could stimulate brown fat. More specifically PPARγ agonistic action can be determined in a similar manner as described above, using a dual luciferase assay with a luciferase construct containing a PPARγ responsive element.

This second compound is not a protein or nucleic acid based compound.

PPARγ is the main target of the drug class of thiazolidinediones (TZDs), used in diabetes mellitus and other diseases that feature insulin resistance. It is also mildly activated by certain NSAIDs (such as ibuprofen) and indoles. Endogenous ligands for these receptors are free fatty acids (FFAs) and eicosanoids. Dual PPARα/γ agonists, so-called glitazars, which bind to both the α and γ PPAR isoforms, are currently under active investigation for treatment of a larger subset of the symptoms of the metabolic syndrome. These include aleglitazar, muraglitazar and tesaglitazar. PPARα is the main target of fibrate drugs, a class of amphipathic carboxylic acids (clofibrate, gemfibrozil, ciprofibrate, bezafibrate, and fenofibrate). They were originally indicated for cholesterol disorders and more recently for disorders that feature high triglycerides. Further, biguanides act in a PPARα dependent matter.

Suitable PPARγ agonists include thiazolidinediones, NSAIDs, sulphonylureas and indoles.

Thiazolidinediones abbreviated as TZDs are also known as glitazones. Suitable thiazolidinediones include rosiglitazone, pioglitazone, troglitazone, and ciglitazone, which are selective ligands for the nuclear transcription factor peroxisome proliferator-activated receptor (PPAR)γ. Typical TZDs have the formula where n is 1, 2, or 3, Y and Z independently are O or NH; and E is a cyclic or bicyclic aromatic or non-aromatic ring, optionally containing a heteroatom selected from oxygen or nitrogen. Suitable TZDs are for example described in WO2000/27401.

NSAIDs are a class of drugs that provides analgesic and antipyretic (fever-reducing) effects, and, in higher doses, anti-inflammatory effects. PPARγ is activated by several endogenous ligands emerging from the metabolism of arachadonic acid and linoleic acid. Among the PPARγ ligands represented are the lipoxygenase products 13(S) HODE (produced from linoleic acid by 15-LOX-1) and 15(S)HETE (produced from arachidonic acid by both 15-LOX-1 and 15-LOX-2, although 15-LOX-2 catalyzes this reaction much more efficiently). Induction of 15-LOX-1 activity by NSAIDs occurs independently of COX-2 inhibition.

NSAIDs can be classified based on their chemical structure or mechanism of action. Older NSAIDs were known long before their mechanism of action was elucidated and were for this reason classified by chemical structure or origin. Newer substances are more often classified by mechanism of action.

Suitable NSAIDs include salicylates, propionic acid derivatives, acetic acid derivatives, enolic acid (oxicam) derivatives and fenamic acid derivatives.

Suitable salicylates include aspirin (acetylsalicylic acid), diflunisal (Dolobid™), salsalate (Disalcid™) and choline magnesium trisalicylate (Trilisate™).

Suitable propionic acid derivatives include ibuprofen, dexibuprofen, naproxen, fenoprofen, ketoprofen, dexketoprofen, flurbiprofen, oxaprozin, and loxoprofen.

Suitable acetic acid derivatives include Indomethacin, tolmetin, sulindac, etodolac, ketorolac, diclofenac and nabumetone (drug itself is non-acidic but the active, principal metabolite has a carboxylic acid group).

Suitable enolic acid (oxicam) derivatives include piroxicam, meloxicam, tenoxicam, droxicam, lornoxicam, and isoxicam.

Suitable fenamic acid derivatives (fenamates) include mefenamic acid, meclofenamic acid, flufenamic acid, and tolfenamic acid.

Sulfonylurea derivatives are a class of antidiabetic drugs that are used in the management of diabetes mellitus type 2. Examples include carbutamide, acetohexamide, chlorpropamide, tolbutamide, tolazamide, glipizide, gliclazide, glibenclamide (glyburide), glibornuride, gliquidone, glisoxepide, glyclopyramide and glimepiride. They act primarily by increasing insulin release from the beta cells in the pancreas. All sulfonylureas contain a central S-phenylsulfonylurea structure with a p-substituent on the phenyl ring (R) and various groups terminating the urea N' end group (R2).

Indoles include indole-derived agents which can bind to PPARγ, and comprise mainly sulfonyl-indoles.

Dual alpha-gamma agonists are suitable as well, and include glitazars.

Suitable glitazars include aleglitazar, muraglitazar and tesaglitazar.

PPARα agonists include fibrates and biguadines.

Fibrates are a class of amphipathic carboxylic acids. They are used for a range of metabolic disorders, mainly hypercholesterolemia (high cholesterol), and are therefore hypolipidemic agents. Fenofibric acid, the active metabolite of fenofibrate, produces reductions in total cholesterol, LDL cholesterol, apolipoprotein B, total triglycerides and glyceride rich lipoproteins.

Suitable fibrates include: bezafibrate (e.g. Bezalip), ciprofibrate (e.g. Modalim), gemfibrozil (e.g. Lopid), fenofibrate (e.g. TriCor).

Biguanides are suitable as well, and suitable biguanides include metformin—which is widely used in treatment of diabetes mellitus type 2—and Proguanil, an antimalarial drug.

The present first and second compound can be formulated in a pharmaceutical dosage form with a pharmaceutically acceptable carrier.

The pharmaceutically acceptable carrier is not limited, but is preferably adapted to the form of the pharmaceutical composition.

The amounts of the three components can vary widely and are mainly determined by the required amounts and effective way of administration.

Preferably, the compound comprising at least one saccharide and at least one sulphate can be present in the pharmaceutical composition such as in an amount of 0-10 wt. % relative to a total weight.

Preferably, the PPARγ agonist can be present in an amount of 0-10 wt. % relative to a total weight.

Preferably, the relative amounts between the two compounds (sulphated compound to PPARγ agonist) are 1:1 to 1:5.

The pharmaceutically acceptable carrier can be present in an amount of 0.01% to 99.9%, preferably 0.1%-10%, and its amount will depend on the formulation.

The invention further relates to the use of said combination as a medicament. The medicament can be in the form of a tablet, capsule, repository, injectable and the like.

In one embodiment, the medicament is in the form of a tablet, suitable for oral administration.

In another embodiment, the medicament is in a form, suitable for local administration.

The medicament can comprise the components in the form of a solid, or liquid preparation.

In a further embodiment of the invention, the combination of above mentioned compounds will be formulated in a form, for example nanoparticle, that depending on its use will be targeted to specific cells, tissues or organs.

The form preferably is a kind of nano-device in which both compounds are packaged for targeted delivery.

Targeting can preferably be done by any specific molecule attached on the outside of the nanoparticle like an antibody, or other molecular or chemical entity that can target specific cells, tissues or organs.

The dosage form can comprise the APIs together, or APIs can be divided over dosage forms, which can be supplied in combination.

The dosage form can be an immediate release or extended release formulation.

The invention furthermore relates to the pharmaceutical composition of the invention for use in the treatment of obesity related disorders like for example coronary artery disease, hypertension, stroke, diabetes, hyperlipidemia and some cancers.

The invention furthermore relates more specifically to the pharmaceutical composition of the invention for the use in the treatment of any one of obesity, diabetes-II, coronary artery disease and hypertension.

In another embodiment of the invention, the invention relates to a method for the inducement of beige/brite and/or brown fat tissue in vitro, by administering an effective amount of the pharmaceutical composition of the invention to mesenchymal progenitor cells, for sufficient period, to induce said BAT. The BAT cells formed can be used to insert in patients at suitable places.

In a further embodiment of the invention, the invention relates to a method for the inducement of BAT in vivo, by administering an effective amount of the pharmaceutical composition of the invention to tissue comprising mesenchymal progenitor cells, for sufficient period, to induce said BAT.

Preferably, the method of inducement of BAT in vivo comprises the administration of the composition of the invention to a pet or mammal comprising said tissue. The pet can be a dog or cat with obesity, the mammal can be a human.

More preferably, the mammal is a human, and the treatment most preferably is performed on human having a BMI higher than 30.

It is an advantage of the present invention, that the constituents of the composition can be non-biologics, and several of the exemplary components are approved medicaments.

Pentosan polysulfate (PPS), manufactured form beechwood, is an FDA-approved oral medication for the treatment of interstitial cystitis (IC), also known as painful bladder syndrome. PPS is known to have anti-inflammatory and pro-chondrogenic properties. Pentosan polysulfate is available as pills or as a direct infusion into the bladder.

Adequan, polysulphated glycosaminoglycan, is a well know veterinary medicament for treating joint pain.

Indomethacin is an FDA-approved, non-steroidal anti-inflammatory drug (NSAID). It's commonly used to reduce fever, pain, stiffness and swelling. Furthermore, Indomethacin is a COX-inhibitor that blocks prostaglandin production and is used as an inhibitor of inflammation. In higher doses it can also induce adipogenesis in vitro in mesenchymal progenitor cells by activating PPARγ.

Pioglitazone is a powerful PPARγ agonist, and belongs to the class of thiazolidinediones, or glitazones, and was designed to treat type II diabetes by increasing the insulin sensitivity.

DETAILED DESCRIPTION OF THE FIGURES

The invention will be elucidated with the following non-limiting examples and experiments.

Figure 2:
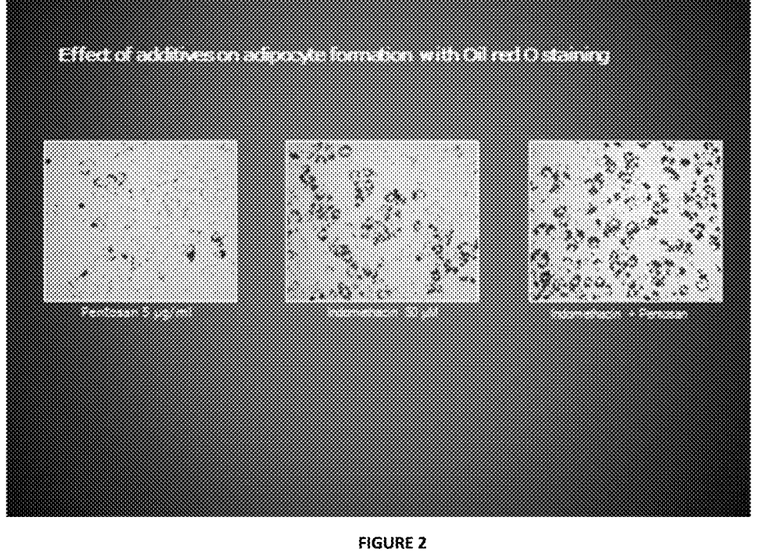
FIG. 2 shows pictures of histological staining experiments, relating to the synergistic effect of the combination of Pentosan with Indomethacin.
Figure 3:
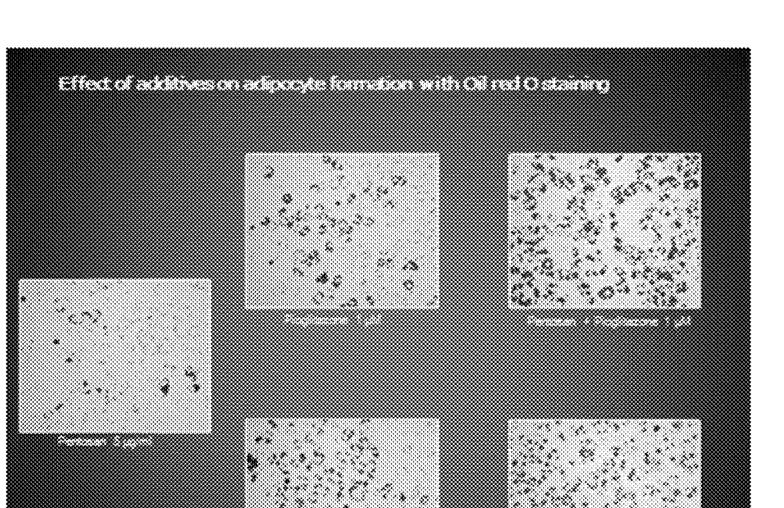
FIG. 3 shows pictures of histological staining experiments, relating to the synergistic effect of the combination of Pentosan with Pioglitazone.
Figure 4:
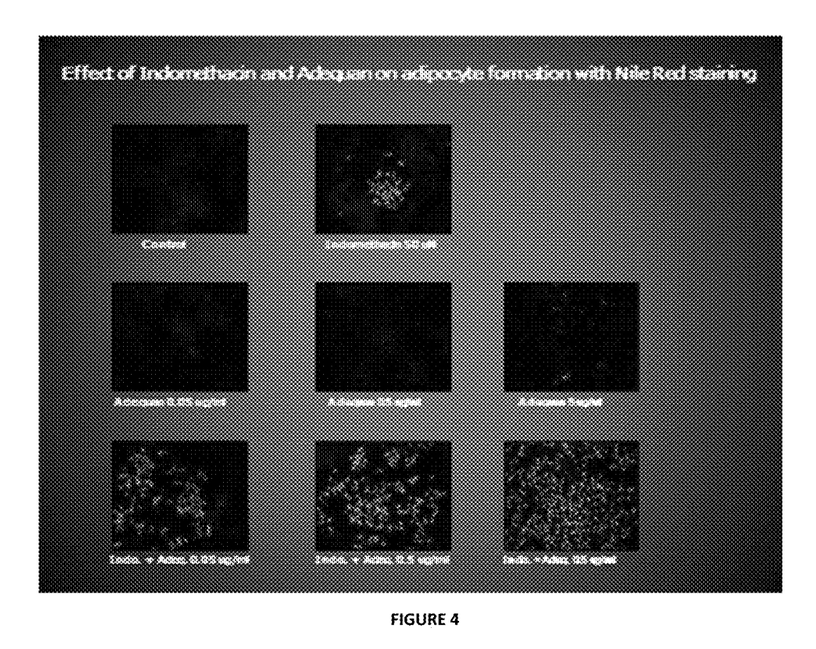
FIG. 4 shows pictures of histological staining experiments, relating to the synergistic effect of the combination of Adequan with Indomethacin.

FIG. 2-4 show the effect of the combined use of a compound comprising a carbohydrate and a sulphate (Adequan or Pentosan), and a PPARγ activator (Indomethacine or Pioglitazone). The concentrations of active compounds used to stimulate the cells are given in the pictures. The active compounds were added to the medium, and thereafter the cells were suspended in the medium. After 3 days, the cells were stained with Oil red O or Nile Red staining.

Oil Red O (Solvent Red 27, Sudan Red 5B, C.I. 26125, $C_{26}H_{24}N_4O$) is a lysochrome (fat-soluble dye) diazo dye used for staining of neutral triglycerides and lipids on frozen sections. The pictures show central nuclei, increasing lipid formation and droplets by the combined use of the composition of the invention, and therefore is indicative of beige adipocyte formation. Nile red (also known as Nile blue oxazone) is a lipophilic stain accumulating in lipid globules inside the cell. Nile Red fluoresces strongly when partitioned into lipids, but practically not at all in aqueous solution.

Figure 5:
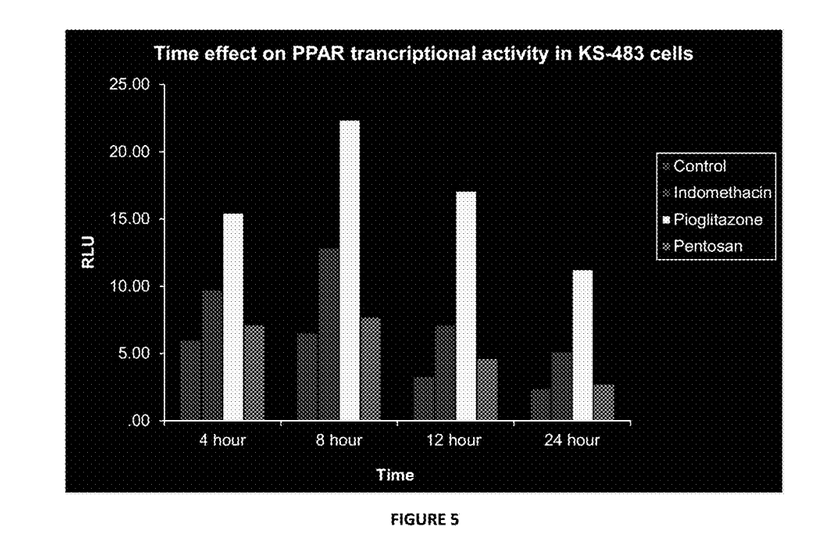
FIG. 5 shows in vitro measurement in relative light units (RLU) of PPAR transcriptional activity in KS-483 cells transfected with a dual PPAR reporter system and exposed to different compounds.

FIG. 5 shows the effect of exposure of KS-483 cells to a compound comprising a carbohydrate and a sulphate (Adequan or Pentosan), and a PPARγ activator (Indomethacine or Pioglitazone).

Examples and Experiments

The genes in KS-483 cells were assessed for up- or downregulation after stimulation with compound. Briefly, KS-483 cells were cultured under standard culturing conditions in α-MEM medium supplemented with glutamax, penicillin/streptomycin and 10% heat-inactivated Foetal Calf Serum (FCS).

For gene-expression analysis cells were seeded at 9210 cells/cm2 in 6-wells culture plates (Costar). At day 4, when cells were confluent, cells were stimulated with compounds in the presence of 5 μg/ml vitamin C. After 72 hours stimulation, cells were washed with PBS and subsequently RNA from the cells was isolated in 1 ml TRIzol (Invitrogen) following a standard TRIzol isolation protocol. RNA concentration and purity was assessed on a Nanodrop 1000 (Thermo Scientific). Single strand cDNA was synthesized from the isolated mRNA using reverse transcriptase (RT). Subsequently, SYBR green real-time PCR, also known as qPCR, was used to quantify differential gene expression of selected genes normalized to the expression of the housekeeping gene beta-2 microglobulin (b2m). SYBR green specifically binds to double-stranded DNA and only fluoresces when bound to DNA, hence during generation of a gene-specific amplicon with gene-specific primers (all from Qiagen) fluorescence increases. The qPCR protocol applied was as follows:

15 minutes at 95° C. to activate Taq DNA polymerase, inactivate reverse transcriptase and denaturate the cDNA template.

40 cycles of 15 seconds denaturation at 95° C., 30 seconds annealing at 55° C. and 30 seconds of extension at 72° C.

Since SYBR green does not distinguish between one DNA and another a melt curve was generated after the PCR program, in which the temperature is raised by a fraction of a degree and the change in fluorescence is measured. At the melting point, the two strands of DNA will separate and the fluorescence rapidly decreases. Presence of multiple melting point, pointing at contaminated end-products was verified.

The threshold cycle or $C_T$ value (the cycle at which a statistically significant increase in normalized fluorescence intensity is first detected) were determined and relative fold change of genes of interest compared to b2m was determined.

The following genes were assessed: Table 1

| Gene | description of gene/protein | Remarks |
| --- | --- | --- |
| PLIN1 | perilipin 1 | Essential for lipid storage and lipolysis |
| CD36 | CD36 antigen, Fatty Acid Translocase (FAT) | Cellular uptake of Fatty Acids = fatty acid transporter, stim mitochondria |
| Fabp-4 | Fatty Acid Binding Protein 4 (also called aP2) | Binds fatty acids, involved in lipolysis and lipogenesis |
| LPL | LipoProtein Lipase | Early differentiation marker, enzyme is made primarily in adipose tissue |
| SLC2A4 | solute carrier family 2 member 4 or GLUT-4, mediates insulin-regulated facilitative glucose transporter | Highly expressed in BAT |
| O3FAR1 | omega-3 fatty acid receptor 1 | Plays a role in inflammation, insulin resistance, obesity and type 2 diabetes mellitus |
| CIDEA | Cell death-inducing DNA fragmentation factor | Highly expressed in BAT, not in WAT |
| CEBP | CCAAT/enhancer binding protein (C/EBP), alpha | Most important factor for regulation of adipogenesis |
| PRDM16 | PR domain containing 16 | Highly enriched in BAT as compared with WAT, plays a role in thermogenic processes, activity of PRDM16 in WAT leads to the production of brown fat-like adipocytes within white adipose tissue, called Brite Cells |
| LRP5 | low density lipoprotein receptor-related protein 5 | Levels are increased during adipocyte differentiation |
| SCD1 | stearoyl-Coenzyme A desaturase 1 | Increased signaling leads to acivation of Ppargc1a and increased uncoupling via UCP-1 |
| Pparγc1α/ PGC-1α | peroxisome proliferative activated receptor, gamma, coactivator 1 alpha | Regulates the genes involved in energy metabolism |
| PPAR-gamma | peroxisome proliferator activated receptor gamma | Transcriptional coactivator for the expression of UCP-1 |
| UCP-1 | UnCoupling Protein 1 | Expressed in mitochondria of brown adipocytes. UCPs separate oxidative phosphorylation from ATP synthesis with energy dissipated as heat, |
| SOX9 | SRY-box containing gene 9 | Acts during chondrocyte differentiation and, with steroidogenic factor 1, regulates transcription of the anti-Müllerian hormone (AMH) gene. |
| Osteocalcin = Bglap | | Transcriptional coactivator for UCP-1 expression, secreted by osteoblasts and thought to play a role in the body's metabolic regulation and is pro-osteoblastic |
| FGF-21 | fibroblast growth factor 21 | regulates PGC-1a and browning of white adipose tissue |
| COX7a1 | cytochrome c oxidase, subunit VIIa 1 | Brown/brite-specific gene, catalyzes the electron transfer from reduced cytochrome c to oxygen |
| CTNNB1 | beta-catenin | Transcriptional coactivator |
| BMP-7 | | Master switch directing differentiation into brown fat cells, cooperating with PRDM16, Plays a part during different phases of adipogenesis |
| CFD | complement factor D (adipsin) | Beige and white adipose cell lines present similar levels of adipogenesis and fat-cell-specific markers e.g. and aP2 and PPARg |
| Adipoq | Adiponectin | Beige and white adipose cell lines present similar levels of adipogenesis and fat-cell-specific markers e.g. and aP2 and PPARg |
| O3FAR1 | omega-3 fatty acid receptor 1 (GRP120) | Can bind unsaturated fatty acids would could lead to adipogenesis |
| UCP-1 | Uncoupling protein 1 | Uncoupling protein, restricted to brown adipose tissue, for heat generation |
| Noggin | | Can directly induce adipogenesis independently of major signals through C/EBP and PPAR-g |
| BMP-2 | Bone Morphogenic Protein 2 | Plays a part during different phases of adipogenesis |
| BMP-4 | Bone Morphogenic Protein 4 | involved in bone and cartilage development, specifically tooth and limb development and fracture repair |
| WNT5a | wingless-related MMTV integration site 5A (non-canonical) | inhibit (via stimulation of SETB1) PPARg transcription, pathway is crucial for lineage determination |

-continued

| Gene | description of gene/protein | Remarks |
| --- | --- | --- |
| WNT6 | wingless-related MMTV integration site 6 | Endogenic inhibitor of brown adipogeneis |
| DKK2 | Dickkopf homolog 2 (*Xenopus laevis*) | interactions with the Wnt signaling pathway. It can act as either an agonist or antagonist of Wnt/beta-catenin signaling, depending on the cellular context and the presence of the co-factor kremen 2 |
| WNT11 | wingless-related MMTV integration site 11 (non canonical) | This protein has been implicated in oncogenesis and in several developmental processes, including regulation of cell fate |
| WNT10a | wingless related MMTV integration site 10a | Endogenic inhibitor of brown adipogenesis |

Results of the compound stimulation were as given in Table II. The control has an expression of 1; values higher than 1 imply up-regulation of the gene; values lower than 1 imply down-regulation of genes. Table II shows a number of genes that are synergistically upregulated; the Table II also comprise upregulated genes that are not necessarily synergistically upregulated.

TABLE II

Most up-regulated genes in KS-483 cells in KS 483 cells, 3 days stimulation

|  | Indo 5 uM | Pentosan 5 ug/ml | Indo + Pentosan |
| --- | --- | --- | --- |
| 1 ng c-DNA |  |  |  |
| PLIN1 | 354.02 | 17.47 | 3057.42* |
| CD36 | 181.5 | 2.60 | 1921.00 |
| FABP-4 | 162.94 | 3.83 | 1540.66 |
| LPL | 4.43 | 2.33 | 35.52 |
| SLC2A4 | 2.09 | 1.07 | 12.16 |
| O3FAR1 | 2.26 | 0.44 | 12.08** |
| CIDEA | 0.95 | 5.50 | 10.37 |
| CEBP | 1.19 | 0.63 | 5.08 |
| PRDM16 | 1.58 | 1.85 | 4.12 |
| LRP5 | 1.58 | 3.27 | 3.97 |
| SCD1 | 1.32 | 0.85 | 3.79 |
| PpargC1α/PGC-1α | 1.15 | 2.09 | 3.55 |
| PPAR-γ | 0.91 | 1.55 | 2.90 |
| 10 ng c-DNA |  |  |  |
| CFD | 413.23 | 40.86 | 1554.08 |
| Adipoq | 251.30 | 32.00 | 1546.10 |
| O3FAR1 | 5.68 | 1.14 | 24.76 |
| CIDEA | 1.86 | 9.19 | 16.25 |
| UCP-1 | 2.18 | 2.85 | 4.45 |
| Noggin | 2.25 | 3.56 | 4.02 |
|  | Indo 5 uM | Pentosan 0.05 ug/ml | Indo + Pentosan |
| BMP-2 | 1.96 | 1.32 | 10.16 |

Most down-regulated genes in KS-483 cells in KS 483 cells, 3 days stimulation

| 1 ng c-DNA | Indo 5 uM | Pentosan 5 ug/ml | Indo + Pentosan |
| --- | --- | --- | --- |
| FGF21 | 2.33 | 0.23 | 0.90 |
| BMP-7 | 1.62 | 0.77 | 0.59 |
| BMP-4 | 0.81 | 0.77 | 0.54 |
| WNT5a | 0.73 | 0.76 | 0.43 |
| WNT6 | 0.83 | 0.16 | 0.11 |
| DKK2 | 1.06 | 0.14 | 0.09 |
| WNT11 | 1.01 | 0.12 | 0.08 |
| WNT10a | 0.92 | 0.03 | 0.01 |

From the up- and downregulated genes, and their activity as described in table 1, it is clear that a composition, comprising (i) a compound comprising at least one carbohydrate and containing at least one sulphate, in combination with (ii) at least one compound that can activate PPARγ synergistically activates a number of genes important for adipocyte formation of the BAT-type, in particular beige/brite cells.

PPAR Transcriptional Activity Measurements

KS-483 cells were seeded at a density of 9210 cells/cm2 in 475 μl in a 24-wells plate (Costar) and cultured until grown at sub confluence (80%).

Following the manufacturer's protocol, after 24 hours, cells were transiently transfected with a dual PPAR Luciferase reporter system (consisting of a Firefly luciferase with a PPAR Responsive element and a consecutive expressing *Renilla* luciferase to correct luciferase measurements for transfection efficiency) to determine the expression of PPAR upon differentiation. Luciferase assay was performed in quadruplicate, according to the protocol of the dual-luciferase reporter assay system (Promega).

Briefly, 100 μl transfection mix consists of 2 μg DNA (0.4 μg PPRE Luciferase, 25 ng *Renilla* luciferase and 1.6 μg plasmid pcDNA), 6 μl FuGENE (Promega) supplemented with serum and penicillin-streptavidin. free medium. After 15 minutes incubation at room temperature, 0.5 μg DNA (25 μl) from the mixture was added to each well.

20 hours after transfection cells were washed with PBS and stimulated with (i) a compound comprising at least one carbohydrate and containing at least one sulphate or with (ii) at least one compound that can activate PPARγ for 4, 8, 12 and 24 hours in α-MEM with 10% heat-inactivated fetal calfs serum (FCS).

After stimulation cells were washed again with PBS, lysed and luciferase activities were determined in 10 μl of cell lysate. Firefly luciferase activity and *Renilla* luciferase activity (SpectraMax L, Molecular devices) were measured. PPAR activating potential on the Firefly luciferase is shown in relative luciferase units compared to the constitutive *Renilla* luciferase.

From the RLU measured after exposure to single compounds it is clear that a composition, comprising (i) a compound comprising at least one carbohydrate and containing at least one sulphate and compounds that can activate PPARγ lead to a significant increase in RLU and hence PPAR transcriptional activity.

The invention has been described by reference to certain embodiments discussed above. It will be recognized that these embodiments are susceptible to various modifications and alternative forms well known to those of skill in the art without departing from the scope of the invention. Accordingly, although specific embodiments have been described, these are examples only and are not limiting upon the scope of the invention, which is defined in the accompanying claims.

REFERENCES

1. Schuchman E H et al. Pentosan Polysulfate: A Novel Therapy for the Mucopolysaccharidoses. PLoS ONE 8(1): e54459 (2013).
2. Wu J. et al. Inhibition of inflammation by pentosan polysulfate impedes the development and progression of severe diabetic nephropathy in aging C57B6 mice. Laboratory Investigation 91: 1459-1471 (2011)
3. Kumagail K et al. Sodium pentosan polysulfate resulted in cartilage improvement in knee osteoarthritis—An open clinical trial. BMC Clinical Pharmacology 10:7 (2010)
4. Ghosh P et al. Pentosan polysulfate promotes proliferation and chondrogenic differentiation of adult human bone marrow-derived mesenchymal precursor cells. Arthritis Res.&Therapy 12: R28 (2010)
5. Cannon B. et al. Brown Adipose Tissue: Function and Physiological Significance. Physiol Rev 84: 277-359 (2004)
6. Sawant A. et al. Noggin Is Novel Inducer of Mesenchymal Stem Cell Adipogenesis. J. Biol. Chem. 287, no 15: 12241-12249 (2012)
7. William P. et al. Wnt6, Wnt10a and Wnt10b inhibit adipogenesis and stimulate osteoblastogenesis through a β-catenin-dependent mechanism. Bone 50: 477-489 (2012)
8. Wu J. et al. Beige Adipocytes Are a Distinct Type of Thermogenic Fat Cell in Mouse and Human. Cell 150: 366-376 (2012)
9. Fisher F. M. et al. FGF21 regulates PGC-1a and browning of white adipose tissues in adaptive thermogenesis. Genes & Development 26: 271-281 (2012)
10. Palsgaard J. et al. Cross-talk between Insulin and Wnt Signa-ling in Preadipocytes. J. Biol. Chem. 287, no 15: 12016-12026 2012
11. Kennell J. A. et al. Wnt Signaling Inhibits Adipogenesis through β-Catenin-dependent and -independent Mechanisms. The Journal of Biological Chemistry 280, no 25: 24004-24010 (2005)
12. Cristancho A. G. et al. Forming functional fat: a growing understanding of adipocyte differentiation. Nat. Rev. Mol. Cell Biol. 12: 722-734 (2011)
13. Rosenwald M. et al. Bi-directional interconversion of brite and white adipocytes. Nature cell boil. 15, no 6: 659-667 (2013).

What is claimed is:

1. A pharmaceutical composition for use as a medicament for the inducement of beige/brite or brown fat tissue in vivo in the treatment of obesity or disorders contributed by obesity comprising a combination of active pharmaceutical ingredients consisting of: (ingredient i) a compound selected from at least one of Pentosan or polysulfated glycosaminoglycan in combination with (ingredient ii) at least one non-protein or non-nucleic acid compound, different from (ingredient i), that can activate PPAR, wherein (ingredient ii) is a PPARγ agonist selected from triglitazone, rosiglitazone, ciglitazone, pioglitazone, or indomethacin.

2. The pharmaceutical composition according to claim 1, wherein the Pentosan, polysulfated glycosaminoglycan or the PPARγ agonist has has anti-inflammatory effect.

3. The pharmaceutical composition according to claim 1, wherein the composition further comprises (iii) at least one pharmaceutically acceptable carrier.

4. The pharmaceutical composition according to claim 1, wherein the active pharmaceutical ingredients are combined in one dosage form.

5. The pharmaceutical composition according to claim 1, wherein the pharmaceutical composition comprises separate dosage forms for individual pharmaceutical active ingredients.

6. The pharmaceutical composition according to claim 1, wherein the composition is suitable for oral administration.

7. The pharmaceutical composition according to claim 6, wherein the composition is in the form of a tablet or capsule.

8. The pharmaceutical composition according to claim 1, wherein the composition is formulated in a form, which, depending on its use, allows targeting to specific cells, tissues or organs.

9. The pharmaceutical composition according to claim 1, wherein the treatment is of obesity or type II diabetes.

10. A method for the inducement of brown or brite/beige or brown fat tissue, for the treatment of obesity or disorders contributed by obesity comprising the steps of: administering to a patient in need thereof an effective amount of a pharmaceutical composition according to claim 1 for a sufficient period, to induce said fat tissue from mesenchymal progenitor cells.

11. The method of claim 10, wherein the patient is a pet or mammal.

12. The method of claim 11, wherein the mammal is a human having a BMI higher than 30.

13. The pharmaceutical composition according to claim 1, wherein (ingredient ii) is indomethacin or pioglitazone.

14. The pharmaceutical composition according to claim 8 wherein the composition is, formulated in the form of nanoparticles.

15. The pharmaceutical composition according to claim 1, wherein the relative amounts between (ingredient i) and (ingredient ii) are 1:1 to 1:5 by weight.

16. A pharmaceutical composition for use as a medicament for the inducement of beige/brite or brown fat tissue in vivo in the treatment of obesity or disorders contributed by obesity, comprising of two active pharmaceutical ingredients: (ingredient i) selected from at least one of Pentosan or polysulfated glycosaminoglycan present in an amount of 0.1-10 wt. % relative to a total weight, in combination with (ingredient ii) at least one non-protein or non-nucleic acid compound, different from (ingredient i), present in an amount of 0.1-10 wt.% relative to a total weight, that can activate PPAR, wherein (ingredient ii) comprises a PPARγ agonist selected from indomethacin or pioglitazone.

17. The pharmaceutical composition according to claim 16, wherein the Pentosan, polysulfated glycosaminoglycan or the PPARγ agonist has anti-inflammatory effect.

18. The pharmaceutical composition according to claim 16, wherein the composition further comprises (iii) at least one pharmaceutically acceptable carrier.

19. The pharmaceutical composition according to claim 16, wherein the active pharmaceutical ingredients are combined in one dosage form.

* * * * *